US009443181B2

(12) United States Patent
Haushalter

(10) Patent No.: US 9,443,181 B2
(45) Date of Patent: *Sep. 13, 2016

(54) METHODS FOR OPTICALLY ENCODING AN OBJECT WITH UPCONVERTING MATERIALS AND COMPOSITIONS USED THEREIN

(71) Applicant: Parallel Synthesis Technologies, Santa Clara, CA (US)

(72) Inventor: Robert C. Haushalter, Los Gatos, CA (US)

(73) Assignee: Parallel Synthesis Technologies, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/446,139

(22) Filed: Jul. 29, 2014

(65) Prior Publication Data

US 2014/0336061 A1 Nov. 13, 2014

Related U.S. Application Data

(63) Continuation of application No. 10/890,530, filed on Jul. 12, 2004, now Pat. No. 8,796,030.

(60) Provisional application No. 60/486,607, filed on Jul. 12, 2003.

(51) Int. Cl.
| | |
|---|---|
| *G01N 33/58* | (2006.01) |
| *C07F 5/00* | (2006.01) |
| *G06K 19/06* | (2006.01) |
| *B82Y 5/00* | (2011.01) |
| *B82Y 10/00* | (2011.01) |
| *B82Y 15/00* | (2011.01) |
| *B82Y 30/00* | (2011.01) |
| *C12Q 1/68* | (2006.01) |
| *G06K 7/12* | (2006.01) |
| *G06K 7/14* | (2006.01) |
| *G06K 19/02* | (2006.01) |

(52) U.S. Cl.
CPC ............. *G06K 19/0614* (2013.01); *B82Y 5/00* (2013.01); *B82Y 10/00* (2013.01); *B82Y 15/00* (2013.01); *B82Y 30/00* (2013.01); *C12Q 1/6825* (2013.01); *G01N 33/588* (2013.01); *G06K 7/12* (2013.01); *G06K 7/1408* (2013.01); *G06K 19/022* (2013.01); *G01N 2458/40* (2013.01); *Y10T 436/13* (2015.01)

(58) Field of Classification Search
CPC .................................................. G01N 2458/40
See application file for complete search history.

(56) References Cited

U.S. PATENT DOCUMENTS

| | | | |
|---|---|---|---|
| 3,250,722 A | 5/1966 | Borchardt | |
| 3,412,245 A | 11/1968 | Halverson | |
| 3,473,027 A | 10/1969 | Freeman et al. | |
| 4,018,635 A | 4/1977 | Ryan et al. | |
| 4,491,620 A | 1/1985 | Joiner, Jr. | |
| 4,816,344 A | 3/1989 | Chiang | |
| 5,043,265 A | 8/1991 | Tanke et al. | |
| 5,329,127 A | 7/1994 | Becker et al. | |
| 5,674,698 A * | 10/1997 | Zarling et al. | ............... 435/7.92 |
| 5,698,397 A | 12/1997 | Zarling et al. | |
| 5,891,656 A | 4/1999 | Zarling et al. | |
| 6,159,686 A | 12/2000 | Kardos et al. | |
| 6,201,989 B1 | 3/2001 | Whitehead et al. | |
| 6,207,130 B1 | 3/2001 | Kareiva et al. | |
| 6,399,397 B1 | 6/2002 | Zarling et al. | |
| 6,403,947 B1 | 6/2002 | Hoyt et al. | |
| 6,500,622 B2 | 12/2002 | Bruchez, Jr. et al. | |
| 6,514,295 B1 | 2/2003 | Chandler et al. | |
| 6,536,672 B1 | 3/2003 | Outwater | |
| 6,537,829 B1 | 3/2003 | Zarling et al. | |
| 6,552,290 B1 * | 4/2003 | Lawandy | ....................... 209/576 |
| 6,692,031 B2 | 2/2004 | McCrew | |
| 7,309,568 B2 | 12/2007 | Oshida et al. | |
| 8,673,107 B2 | 3/2014 | Haushalter | |
| 8,796,030 B2 | 8/2014 | Haushalter | |
| 8,927,892 B2 | 1/2015 | Haushalter | |
| 2001/0049101 A1 | 12/2001 | Brogger et al. | |
| 2002/0022273 A1 | 2/2002 | Empedocles et al. | |
| 2002/0025490 A1 | 2/2002 | Shchegolikhin et al. | |
| 2002/0041372 A1 | 4/2002 | Gardner et al. | |
| 2003/0002029 A1 | 1/2003 | Dukler et al. | |

(Continued)

FOREIGN PATENT DOCUMENTS

| | | |
|---|---|---|
| EP | 1491350 A2 | 12/2004 |
| WO | 2006047621 A1 | 5/2006 |
| WO | 2007051035 A1 | 5/2007 |

OTHER PUBLICATIONS

"Notice of Allowance", dated Jun. 20, 2014, issued in parent U.S. Appl. No. 10/890,530.
"Final Office Action", dated Mar. 13, 2009, issued in Parent U.S. Appl. No. 10/890,530.
"Office Action", dated Jul. 21, 2010, issued in parent U.S. Appl. No. 10/890,530.
"Final Office Action", dated Dec. 13, 2011, issued in parent U.S. Appl. No. 10/890,530.
"Non Final Office Action", dated Mar. 30, 2011, issued in parent U.S. Appl. No. 10/890,530.
"Non Final Office Action", dated Apr. 24, 2014, issued in parent U.S. Appl. No. 10/890,530.
"Non Final Office Action", dated Jun. 21, 2013, issued in parent U.S. Appl. No. 10/890,530.

(Continued)

*Primary Examiner* — Paul Hyun
(74) *Attorney, Agent, or Firm* — Kaplan Breyer Schwarz & Ottesen, LLP

(57) ABSTRACT

The present invention relates generally to encoding samples. More specifically, it relates to barcodes and compositions involving upconverters and methods including them. In a composition aspect of the invention, a composition comprising two or more lanthanide materials is provided. Each lanthanide material comprises a host, an absorber, and an emitter, and the materials emit detectable electromagnetic radiation upon excitation with absorbable electromagnetic energy. One or more relative ratios of emission intensities uniquely identify the composition.

25 Claims, 2 Drawing Sheets

(56) References Cited

U.S. PATENT DOCUMENTS

| | | |
|---|---|---|
| 2003/0098357 A1 | 5/2003 | Cummings et al. |
| 2003/0129296 A1 | 7/2003 | Kelso |
| 2003/0180482 A1 | 9/2003 | Narita et al. |
| 2003/0207331 A1 | 11/2003 | Wilson et al. |
| 2004/0072233 A1 | 4/2004 | Kauvar et al. |
| 2004/0099740 A1 | 5/2004 | Chresand et al. |
| 2004/0217298 A1 | 11/2004 | Bawendi et al. |
| 2004/0217364 A1 | 11/2004 | Tarsa et al. |
| 2005/0056183 A1 | 3/2005 | Meshirer |
| 2005/0208543 A1 | 9/2005 | Vann et al. |
| 2007/0011023 A1 | 1/2007 | Silverbrook |
| 2007/0059705 A1 | 3/2007 | Lu et al. |
| 2009/0117340 A1 | 5/2009 | Halfyard et al. |
| 2015/0192522 A1 | 7/2015 | Haushalter |

OTHER PUBLICATIONS

"Non Final Office Action", dated Jul. 28, 2008, issued in parent U.S. Appl. No. 10/890,530.

"Non Final Office Action", dated Oct. 29, 2009, issued in parent U.S. Appl. No. 10/890,530.

"International Search Report and Written Opinion", dated Feb. 14, 2007, issued in counterpart International Application No. PCT/US2005/024174.

"Decision to refuse a European Patent Application", dated Oct. 25, 2003, issued in Related EP Application No. 05813069.1 (counterpart to U.S. Appl. No. 11/577,697).

"Summons to attend oral proceedings pursuant to Rule 115(1) EPC", dated May 3, 2013, issued in related EP Application No. 05813069.1 (counterpart to U.S. Appl. No. 11/577,697).

"European Examination Report", dated Oct. 5, 2011, issued in related EP Application No. 05813069.1 (counterpart to U.S. Appl. No. 11/577,697).

"Extended European Search Report", dated Aug. 5, 2009, issued in related EP Application No. 05813069.1 (Counterpart to U.S. Appl. No. 11/577,697).

"International Search Report and Written Opinion", dated Apr. 4, 2006, issued in related International Application No. PCT/US2005/038638 (counterpart to U.S. Appl. No. 11/577,697).

"Office Action", dated Apr. 26, 2012, issued in related U.S. Appl. No. 11/577,697.

"Office Action", dated Jun. 27, 2014, issued in related U.S. Appl. No. 11/577,697.

"Office Action", dated Aug. 30, 2013, issued in related U.S. Appl. No. 11/577,697.

"Notice of Allowance", dated Sep. 2, 2014, issued in related U.S. Appl. No. 11/577,697.

"Supplemental Notice of Allowance", dated Sep. 18, 2014, issued in related U.S. Appl. No. 11/577,697.

Office Action, dated Dec. 15, 2011, issued in related U.S. Appl. No. 12/091,900.

"Notice of Allowance", dated Oct. 25, 2013, issued in related U.S. Appl. No. 12/091,900.

"Office Action", dated Sep. 17, 2012, issued in related U.S. Appl. No. 12/091,900.

"Office Action", Apr. 22, 2011, issued in related U.S. Appl. No. 12/091,900.

"Office Action", dated Apr. 26, 2010, issued in related U.S. Appl. No. 12/091,900.

"International Search Report and Written Opinion", dated Feb. 21, 2007, issued in related International Application No. PCT/US2006/042359.

"Definition of 'print'"—Merriam-Webster Dictionary; Dec. 2011.

W. H. Wright, et al, "Flow cytometry with upconverting phosphor reporters", Apr. 1998, pp. 245-254, vol. 3260, Publisher: SPIE Proceedings, Published in: US.

Simon Officer et al, "Novel online security system based on rare-earth doped glass micro beads", "The International Society for Optical Engineering", Jan. 20, 2004, pp. 387-395, vol. 5310, No. 1, Publisher: SPIE, Published in: US.

Matthew J. Dejneka et al., "Rare earth-doped glass microbarcodes", "National Academy of Science", Jan. 21, 2003, pp. 389-393, vol. 100, No. 2, Publisher: National Academy of Sciences of USA, Published in: US.

"Non Final Office Action" dated Feb. 4, 2016, issued in related U.S. Appl. No. 14/530,074.

\* cited by examiner

METHODS FOR OPTICALLY ENCODING AN OBJECT WITH UPCONVERTING MATERIALS AND COMPOSITIONS USED THEREIN

RELATED APPLICATIONS

This application is a continuation of U.S. patent application Ser. No. 10/890,530, entitled METHODS FOR OPTICALLY ENCODING AN OBJECT WITH UPCONVERTING MATERIALS AND COMPOSITIONS USED THEREIN, filed Aug. 5, 2014, which claims priority under 35 U.S.C. §119 to U.S. Provisional Application No. 60/486,607 entitled METHODS FOR SAMPLE LABELING WITH UPCONVERTING PHOSPHORS, filed Jul. 12, 2003, which applications are hereby incorporated-by-reference in their entirety.

FIELD OF INVENTION

The present invention relates generally to optically encoding objects. More specifically, it relates to optical barcodes and compositions involving upconverting phosphors and methods and apparatus relating to them.

BACKGROUND

The authentication of objects (e.g., documents, money or pharmaceuticals) has been an important endeavor for thousands of years. It will, similarly to encryption and code breaking, continue to be a significant and constantly evolving problem for the indefinite future. While a great deal of effort has been expended with respect to the development of Information Technology related security issues, the physical encoding of samples to identify, track and validate objects or samples is also critically important. The considerable financial and physical losses that result from counterfeiting and the lack of widespread, accurate and inexpensive authentication technology permeate every aspect of society. Examples include document forgeries, illegal duplication of software and optical media, branded consumer goods, technical intellectual property theft and pharmaceutical tampering.

One method to identify objects is to optically encode them, which is to say that an object combined with an optically active material can be identified by emitting a unique spectral or optical signal or signature upon undergoing suitable excitation. Previously known systems for optically encoding objects or samples have a fundamental problem: they cannot support a very large number of unique codes which means only small numbers of samples can be measured. A unique identifying code is related to a unique optical emission signature. In nearly all cases, the optical code is generated by observing ratios of two or more emitting components in a mixture. However, if the emitters are organic dyes or quantum dots, their short, excited state lifetimes lead to broad emission peaks, each of which can occupy a large swath of the visible spectrum. Therefore, when two or more components are mixed to create a desired ratio that emits a code of interest, it is difficult to deconvolute the broad overlapping peaks. This is starkly reflected in that the most extensive, commercially available code currently consists of only two dyes resolvable at 1% compositional intervals giving a maximum of 100 samples that can be labeled uniquely.

Therefore, there exists a significant need in the art for a method of optically encoding an object or sample such that truly large numbers of codes can be obtained and used to encode very large numbers of objects or samples which can then be uniquely identified.

SUMMARY OF INVENTION

The present invention provides compositions, methods, and apparatuses.

In a composition aspect of the invention, a composition comprising two or more lanthanide materials is provided. Each lanthanide material comprises a host, an absorber, and one or more emitters, and the materials emit detectable electromagnetic radiation upon excitation with absorbable electromagnetic energy. One or more relative ratios of emission intensities uniquely identify the composition.

In another composition aspect of the invention, a composition comprising a lanthanide material is provided. The lanthanide material comprises a host, an absorber and two or more emitters, and the material emits detectable electromagnetic radiation upon excitation with absorbable electromagnetic energy. One or more relative ratios of emission intensities uniquely identify the composition.

In a method aspect of the invention, a method of optically encoding an object is provided. The method comprises combining the object with a composition comprising two or more lanthanide materials, and each lanthanide material comprises a host, an absorber and one or more emitters. The materials emit detectable electromagnetic radiation upon excitation with absorbable electromagnetic energy, which is optically analyzed and the data treated to generate the unique identifying optical barcode.

In another method aspect of the invention, a method of optically encoding an object is provided. The method comprises combining the object with a composition comprising a lanthanide material, and the lanthanide material comprises a host, an absorber and two or more emitters. The material emits detectable electromagnetic radiation upon excitation with absorbable electromagnetic energy which is optically analyzed and the data treated to generate the unique identifying code.

In an apparatus aspect of the invention, an apparatus for identifying an object is provided. The object is combined with a composition of the present invention, and the apparatus includes: an infrared laser diode for exciting the materials; at least one detector, wherein the detector comprises at least one photomultiplier tube or at least one charge-coupled device, for measuring the detectable electromagnetic radiation emitted from the materials; and, a means of rapidly moving the samples past the detector; and, a processing unit for quantifying the emitted, detectable electromagnetic radiation, calculating the one or more relative ratios of emission intensities, assigning a unique code to all calculated relative ratios, and reading the unique codes to identify the object. The apparatus is capable of temporally resolving the emission from the composition of the present invention from emissions from organic dye and quantum dot reporters.

DETAILED DESCRIPTION

Figure 1:
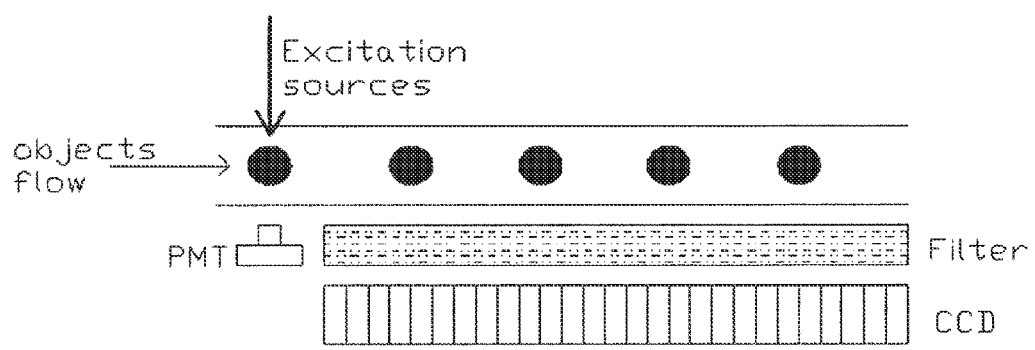
FIG. 1 shows an apparatus to rapidly measure optical cods of the present invention in a flow cytometer setting.

"Optical Barcode" refers to an object or composition that has a unique optical spectrum.

"Reporter" refers to a chemical substituent attached to a probe that produces, under appropriate excitation conditions, a detectable optical signal, wherein the signal indicates the presence of the probe.

"Target" refers to an object that can be assayed using various methods. Examples of targets include, without limitation, polypeptides, glycoproteins, viruses, microorganisms, polynucleotides and pharmaceuticals.

"Probe" refers to a binding component that binds preferentially to one or more targets (e.g., antigenic epitopes, polynucleotide sequences, macromolecular receptors) with an affinity sufficient to permit discrimination of reporter-probe combination to target from a nonspecifically bound reporter-probe combination (i.e., background).

"Lanthanide Materials" refers to materials containing elements 57-70.

"Rare Earth Upconverting Phosphor (RUP) Materials" "Upconverting composition", "upconverting material", "lanthanide upconverter", or "upconverter" refer to upconverting phosphor materials containing rare earths or lanthanides. A general upconverting phosphor composition includes a host, one or more absorbers, which are sometimes referred to as sensitizers, and one or more emitters. The host or host lattice is the parent structure or structure type into which the absorbers and emitters are incorporated, generally in the form of a solid solution. A solid solution is a lattice into which different chemical constituent substitutes randomly and isomorphously into the parent host lattice. The absorbers in an upconverting composition contain species that absorb the appropriate excitation energy and then transfer two or more photons of this absorbed energy to the emitter species, which release energy from the multiphoton absorption in the form of visible light. An exemplary rare earth upconverting phosphor composition is $(Y_{2-x-y}Yb_x[(RE_1)_a(RE_2)_b(RE_n)_c]O_2S$, where $(a+b+\ldots c)=y$ and RE is an emitter chosen from the group $Er^{3+}$, $Ho^{3+}$, $Tm^{3+}$, $Pr^{3+}$, $Nd^{3+}$, and $Dy^{3+}$. In this example, $Y_2O_3$ is the host material, $Yb^{3+}$ is the absorber, and $RE_n$ is one of the rare earth emitters.

"Thermolysis" refers to the thermal decomposition of molecular or polymeric precursors into a solid state material (e.g., yttrium nitrate thermolyzing to yttrium oxide plus nitrogen oxides).

The present invention provides an optical encoding method that far exceeds current technology in terms of accuracy, depth of multiplexing and speed, as well as the number of unique and usable barcodes and compositions used in the method. The method involves the use of more than one upconverting lanthanide material, preferably the use of more than one Rare earth Upconverting Phosphor material. Optionally, the upconverting materials may be combined with fluorescent dyes or quantum dots to increase the number of available codes.

Host materials may include, without limitation, sodium yttrium fluoride ($NaYF_4$), lanthanum fluoride ($LaF_3$), lanthanum oxysulfide, yttrium oxysulfide, yttrium fluoride ($YF_3$), yttrium gallate, yttrium aluminum garnet, gadolinium fluoride ($GdF_3$), barium yttrium fluoride ($BaYF_3$, $BaY_2F_5$), and gadolinium oxysulfide. Absorber/emitter combination examples are ytterbium/erbium, ytterbium/thulium, and ytterbium/holmium, erbium/thulium although others may also be used.

In the present invention, the absorber is preferably ytterbium, erbium or samarium and the emitting centers are preferably erbium, holmium, terbium, thulium, praseodymium, neodymium or didymium. Usually, the molar ratio of absorber:emitting center is at least 1:1, with ratios of at least 3:1 to 5:1 being more common. Preferably, the ratio is at least 8:1 to 10:1, more preferably at least 11:1 to 20:1. The ratio typically is less than 250:1, preferably less than 100:1, and more preferably less than 50:1 to 25:1.

The optimum ratio of absorber (e.g., ytterbium) to emitting center (e.g., erbium, thulium, or holmium) varies, depending upon the specific absorber/emitter couple. For example, the absorber:emitter ratio for Yb:Er couples is typically in the range of about 20:1 to about 100:1, whereas the absorber:emitter ratio for Yb:Tm and Yb:Ho couples is typically in the range of about 500:1 to about 2000:1. For most applications, up-converting phosphors may conveniently comprise about 10-30% Yb and either: about 1-8% Er, about 0.5-0.001% Ho, or about 0.5-0.001% Tm and 0.5-001 for Pr.

Exemplary formulae for upconverting phosphor materials include, without limitation, the following: $Na(Y_xYb_yEr_z)F_4$, where x is 0.7 to 0.9, y is 0.09 to 0.29, and z is 0.05 to 0.01; $Na(Y_xYb_yHo_z)F_4$, where x is 0.7 to 0.9, y is 0.0995 to 0.2995, and z is 0.0005 to 0.001; $Na(Y_xYb_yTm_z)F_4$, where x is 0.7 to 0.9, y is 0.0995 to 0.2995, and z is 0.0005 to 0.001; and, $(Y_xYb_yEr_z)O_2S$, where x is 0.7 to 0.9, y is 0.05 to 0.12; and z is 0.05 to 0.12.

Preferable formulae for upconverting Phosphor materials include, without limitation, the following: $[(Y_{0.8}Yb_{0.19}(RE)_{0.01})_2O_2X$, X=O or S], with RE=Tm, Er, Ho, Pr, Nd and Dy. Elements Tm, Er, Ho, Pr, Nd and Dy act as the emitters, and Yb acts as a sensitizer for 980 nm excitation; and, $Na(Y_xYb_y(RE)_z)F_4$ with RE=Tm, Er, Ho, Pr, Nd and Dy. Elements Tm, Er, Ho, Pr, Nd and Dy act as the emitters, and Yb acts as a sensitizer for the 980 nm excitation Typically, the dyes that are optionally included with the upconverting materials are fluorescent organic dye molecules. Examples of such dyes include, without limitation, the following: rhodamines, cyanines, xanthenes, acridines, oxazines, porphyrins, and phthalocyanines.

Quantum dots are tiny nanocrystals composed of periodic groups of II-VI, III-V, or IV-VI materials that range in size from 2-10 nanometers or roughly the size of 10 to 50 atoms in diameter. Typically, quantum dot cores are composed of cadmium sulfide (CdS), cadmium selenide (CdSe), or cadmium telluride (CdTe). The semiconductor material used for a particular size core is chosen based upon the emission wavelength range being targeted: CdS for UV-blue, CdSe for the bulk of the visible spectrum, CdTe for the far red and near-infrared. These cores can be synthesized as nano-sized ($10^{-9}$ meters) spheres, rods, pyramids, boomerangs, tetrapods, or many other shapes. Typically, spherical particles or slightly elongated ellipsoidal (rod-like) materials are used.

The upconverting materials may either be physically mixed to form a solid or included within a particle. While one may use any suitable particle material in the present invention, glass microspheres are preferred. One preferred method for the fabrication of the encoded glass beads involves impregnation of a porous glass microsphere with a solution comprised of the appropriate type and amounts of soluble lanthanide compounds followed by dehydration and thermolysis of precursor into a solid state material. An example would be the thermal decomposition of yttrium nitrate to yttrium oxide carried out by heating the compound from room temperature to a suitably high temperature. The impregnation of glass beads typically involves the following steps: an appropriate metal nitrate solution is used to fill the pores of the glass beads. Controlled Pore Glass (CPG) beads, which are commercially available with large surface areas (10-100 $m^2 \cdot g^{-1}$) and relatively monodisperse pore sizes ranging from 10-300 nm, readily imbibe aqueous solutions. To prepare an oxide based lanthanide material, aqueous solutions containing the correct molar ratios of cation precursor for the host, one or more absorbers and one or more emitters. For example to prepare $[(Y_{0.8}Yb_{0.19}Ho_{0.01}]_2O_3$ by this procedure, an aqueous solution of the nitrates of Y, Yb and Ho are prepared, mixed and imbibed into the pores of the correct amount of CPG. The beads are subsequently freeze dried, which avoids any possible phase segregation due to preferential crystallization; and, the desiccated materials are rapidly heated to a temperature that decomposes the nitrates into insoluble, solid state RUP oxide materials inside the pores of the beads. Since the constituent components are atomically mixed in solution, and there is no possible demixing mechanism, the beads will identically reflect the solution concentration.

Another preferred method for the preparation of the lanthanide materials of the present invention is spray drying and spray pyrolysis. The mixed lanthanide solutions as above are nebulized into fine droplets (~10 microns) with, for example, an ultrasonic nebulizer and carried with a gas stream into a region of sufficiently high temperature to create the solid state material of interest.

Yet another preferred method for the synthesis of the lanthanide materials of the present invention is flame spray pyrolysis whereby the appropriate ratios of lanthanide materials are prepared, for example, in the form of their perfluoroacetonylacetonate complexes, dissolved in an organic solvent and mixed with $O_2$ in a torch an burned to the oxide much as in the commercial production of flame spray silica.

Still another preferred method for the synthesis of the lanthanide materials of the present invention is combustion synthesis. For example, $(Y_{0.8}Yb_{0.19}Ho_{0.01})_2O_2S$, is prepared by the mixing the appropriate molar ratios of anhydrous Y, Yb and Ho nitrates with dithiooxamide $(CSNH_2)_2$, and heating to the ignition point whereupon the ensuing deflrative combustion reaction forms the desired oxysulfide.

Still another preferred method for the synthesis of the lanthanide materials of the present invention is using Physical Vapor Deposition (PVD) techniques (e.g. pulsed laser depositing, sputtering, e-beam, thermal evaporation) to apply the lanthanide materials as a series of layers deposited onto the object or sample to be encoded.

An additional preferred method for the synthesis of the lanthanide materials of the present invention is to repeatedly heat the appropriate amounts of the constituent binary oxides, interspersed with grinding steps, to 1500° C. until the reaction is complete.

The upconverting materials of the present invention are used to encode a variety of samples or objects. Such samples/objects include, without limitation, paper documents, optical media, automobile components, humans or animals, food packaging, pharmaceutical preparations, and biological samples. Where paper documents are encoded, the documents are impregnated with colloidal dispersions of the materials by printing, dipping or spraying. Encoding optical media typically involves casting the upconverting materials directly into the polymer used to make the media.

For biological samples, upconverter containing particles are typically incorporated into or attached to the sample. The sample may be any sort of biomolecule, with DNA being a particularly preferred sample. Where the particle is a glass bead, DNA is usually attached to it through a series of steps.

First, trisethoxy-n-propylsilylamine is reacted with the Si—OH groups of the glass surface. Protonation of the aminated surface generates a polycationic substrate. Addition of polyanionic DNA to the substrate results in attachment through a series of ionic bonds. The multiple ionic bonds ensure that the attachment can withstand a variety of mechanical and solvent-induced forces.

DNA, RNA proteins and polypeptides may be attached to the optically encoded materials of the present invention through a series of chemical reactions to attached the biological molecules to the encoded materials through covalent bonds. For example to attach a protein to a RUP particle, the RUP particles can be coated with silica by treating the particles with a solution of $Si(OCH_2CH_3)_4$ and subjecting the mixture to hydrolysis. Next, the silica surface of the particle is aminated as above and crosslinked to the protein with glutaraldehyde.

Sample detection using a method of the present invention involves excitation of the upconverter lanthanide materials. The two or more upconverters absorb at least two photons at a particular wavelength and subsequently emit electromagnetic energy at an emission wavelength lower than the excitation wavelength. The intensity of the each excited upconverter emitter's emission is measured, and the ratios of the intensities are calculated. One or more of these ratios constitute a code that distinctly identifies the sample.

The method is further illustrated through a description of a two upconverter system with five distinguishable emission intensities. If each emission intensity is given a designation of 1, 2, 3, 4 or 5, then twenty-five different combinations can result. This is shown below in Table 1.

TABLE 1

| 1, 1 | 1, 2 | 1, 3 | 1, 4 | 1, 5 |
| 2, 1 | 2, 2 | 2, 3 | 2, 4 | 2, 5 |
| 3, 1 | 3, 2, | 3, 3 | 3, 4 | 3, 5 |
| 4, 1 | 4, 2 | 4, 3 | 4, 4 | 4, 5 |
| 5, 1 | 5, 2 | 5, 3 | 5, 4 | 5, 5 |

Assuming that each cell of Table 1 represents a sample with a corresponding particle, one can measure intensity at two different emission wavelengths, take the ratio of the wavelengths, and distinguish (i.e., read the code of) twenty-one of the twenty-five samples from one another. One can only distinguish fewer than twenty-five codes, because some of the codes (i.e., 1,1/2,2/3,3/4,4/5,5; 1,2/2,4; etc.) are redundant: the ratio in each case is equal to 1.

If desired, sample redundancy can be removed in two different ways. If one can measure the absolute intensity at the two emission wavelengths, then the code "1,1" can be distinguished from "3,3," for instance. In contrast, if one includes an internal standard in a sample, then one can ascertain emission intensity through comparison to it. All twenty-five codes can be read in either case.

The simple case of a binary mixture of upconverting materials (e.g., RUP materials) is used to encode a sample, emission intensities can be finely distinguished, which drastically increases the number of available codes. For instance, given a binary mixture of two RUP materials designated $A_xB_{x-1}$, where x is a value between 0 and 1, ratios can be optically differentiated at intervals of less than 0.3% (i.e., x varies in 0.003 increments) at a $2\sigma$ confidence level. This means that greater than 300 separate ratios can be detected and resolved. Accordingly, where a ternary mixture of upconverting materials having different emission wavelengths is used, about 90,000 samples can be distinguished;

a quarternary mixture allows the identification of about $3\times10^7$ samples; and, a quintary mixture provides for the identification of a staggering $6\times10^9$ samples at a similar resolution of ratios.

The addition of a single fluorescent dye, for example, to a mixture of upconverting materials doubles the number of identifiable samples. In other words, inclusion of a red dye with a binary mixture of RUP materials provides for about 600 different codes; inclusion with a ternary mixture provides for about 180,000 different codes. Combination with quantum dots, which come in 4 commercially available colors, would accordingly quadruple the identification capability of the method.

The detection and code-reading related to the upconverting materials (e.g., RUP materials) is generally performed in a series of steps. First, the target sample is illuminated with electromagnetic radiation at an excitation wavelength. For particles containing at least two upconverting phosphor materials, samples are typically excited by radiation of 960 nm to 1000 nm, preferably 970 nm to 990 nm, and more preferably about 980 nm. Second, radiation at two or more emission wavelength bands is detected. Excited phosphors, for instance, emit radiation in the 400 nm to 800 nm range, which is in the visible range. At least one ratio of emission band intensities is calculated. The obtained ratio provides a unique code if the absolute intensities are known; or, one compares the ratio to an internal standard, which provides the unique set of codes.

Any suitable excitation source may be used, including infrared laser diodes and incandescent filaments. Undesirable wavelengths from the source illumination may be filtered from the detector using optical filters that have low transmissibility for the excitation wavelength. The excitation illumination may also be multiplexed and/or collimated, for example through the use of a dichroic mirror array. This would allow the simultaneous excitation of multiple upconverter species having different excitation wavelength bands. The illumination may be continuous or pulsed or a combination of the two. Such a combination would allow signal discrimination between continuous wave induced and pulsed phosphorescence. Once can accordingly discriminate between multiple phosphor species having similar emission spectra but different excitation spectra.

The less than 800 nm radiation from excited upconverting materials can be detected and quantified in a number of ways using visible absorption spectroscopy. Examples of detecting means include, without limitation, photomultiplier tubes (PMTs), avalanche photodiode, charge-coupled devices (CCD), CID devices, or arrays of these devices, photographic film emulsion, photochemical reactions yielding detectable products, and visual observation (e.g., fluorescent light microscopy). Residual background noise in the detection can be decreased through the use of time-gated and/or frequency-gated light collection. RUPs typically have emission lifetimes on the order of a few milliseconds, which is in contrast to the 100 ns decay of background noise. This makes the use of time-gated detection desirable when using a pulsed excitation source.

Where the method of the present invention is used to encode samples of a biological assay, excitation, detection and quantification is oftentimes performed using a flow cytometer. Flow cytometers (FC) have been used in conjunction with upconverting phosphor materials, as described in the following publications, each of which is incorporated-by-reference for all purposes: US published Pat. Appl. 20030207331; U.S. Pat. Nos. 6,537,829; 6,399,397; 6,159,686; 5,891,656; 5,674,698; 5,698,397; and, Flow Cytometry with Upconverting Phosphors Reporters" by W. H. Wright et al. in SPIE Proceedings: Optical Investigations of Cells In Vitro and In Vivo, D. L. Farkas et al. (editors), Vol. 3260, published April 1998, pp. 245-254.

For certain applications, such as gene expression, high sample throughput using a flow cytometer depends not only on the quality and multiplexing depth of the encoding system; it also depends on the means to optically evaluate particles very rapidly. In order for the system to display maximum utility, the encoding system must interfere with as few preexisting, standard assays as possible. For gene expression in particular, the encoding system cannot interfere with a standard cy3/cy5 organic dye combination, which is used to determine the sample and control DNA ratios in hybridization experiments. This can be problematic as there is a great deal of spectral overlap between the RUP and the cy3/cy5 emitters.

The above-described problem can be overcome by taking advantage of the large difference in excited state lifetimes of RUP and organic emitters. This is done by temporally resolving two emission types using a fast, intensified CCD and the rapid flow inherent in the flow cytometer. By judicious choice of the particle size, flow rate, length of detection region and detector rise time, resolution and frame rate, many "snapshots" of the particles moving past the CCD pixels can be obtained and the intensity summed from each pixel to measure the entire emission profile. The temporal resolution scheme is predicated on the fact that typical organic emitters have excited state lifetimes of 1-10 ns while the RUP emitters have much longer characteristic corresponding lifetimes of ~10 ms for $Er^{3+}$, ~2 ms for $Yb^{3+}$, ~1 ms for $Eu^{3+}$, ~0.1 ms for $Dy^{3+}$, ~0.3 ms for $Tb^{3+}$ for example. These lifetimes are directly related to emission peak width and this is what allows the RUP materials with narrow emission bands to be multiplexed so deeply, and why the organic based emission is very broad by comparison.

The FC flow rate is adjusted to the decay time of bead emission and detector size to ensure that 70% or 80% of its emission is collected by a linear CCD with high sensitivity or an array of PMT as the bead passes the CCD or PMT. The next bead enters the CCD which is triggered by the PMT to start next frame. By adjusting the frame readout rate of the CCD, the decay time of RUP emission is measured.

Based on this data, the flow rate is increased to allow more beads pass the CCD per second. Each frame triggered by PMT digitizes all emission intensities of all beads which are in the view of CCD during the exposure time. The exposure time is the dwell time of each bead at each pixel. The sampling rate is the frame rate. All frame data is transferred to a computer and is analyzed to show the emission in real-time. An apparatus comprising the necessary components to very rapidly measure the RUP optical barcodes in a flow cytometer setting is shown in FIG. 1.

For example, beads at a speed of 10 $ms^{-1}$ labeled with $Er^{3+}$, which has the longest decay time (1 ms) of any of the RE ions used, passes a linear CCD of 1028 pixels. Each bead stays at one pixel for 7.8 μs, which is the exposure time. The interframe time is set to 100 ns. Therefore 1280 particles a spacing of 78 μm are resolvable in one frame. If frame rate is 128 Kfps, then 128,000 beads are counted in one second. This data volume equals one frame of an area CCD with 1280×1024 pixels. It is therefore possible to resolve and detect $8\times10^7$ beads in one second. Beads with a shorter excited state lifetime can be read even faster.

EXAMPLES

The following example illustrates how the emission from a rare earth center in a RUP based material can provide the desired degree of multiplexing in rare earth upconverting phosphors and two photon upconversion processes. In certain embodiments disclosed here, Ytterbium is the absorber and various other trivalent rare earth ($RE^{3+}$) cations such as Tm, Pr, Ho, Dy, Er, Eu, Ce, Nd, Sm and Tb constitute the RUP emitter material. In other embodiments the absorber is Er. The $Yb^{3+}$ cations absorb two ~980 nm infrared photons and the combined energy from two of the photons is transferred to one of the emitting cations which reemits the energy as visible photons. The Er absorbers absorb in the vicinity of 1500 nm. This so-called multi-photon upconversion process, which converts infrared energy to visible light, is a nonlinear optical process and the output power increases more than linearly with increasing excitation power. In addition to the two photon upconversion process, upconversion can also take place with three, four or more photons although to a lesser extent than the two photon processes.

It will be understood by those skilled in the art that in addition to the examples disclosed here, there are a very large number of other types of objects or samples that can be encoded, other combinations of reporters to combine with the RUP materials and other rare earth absorbers and emitters that can be used in a fashion similar to the embodiments disclosed here. The following examples are not meant to limit the scope of the invention in any way whatsoever.

Example 1

A Composition Comprising Two or More Lanthanide Materials, Wherein Each Lanthanide Material Comprises a Host, an Absorber, and One or More Emitter Example 1 demonstrates how intensity ratio measurements within a series of variable emitter RUP materials can provide the desired degree of multiplexing for encoding very large numbers of objects. The results of this experiment demonstrate that a binary mixture of two RUP materials can be optically differentiated at intervals of 0.3% at a $2\sigma$ confidence level; in other words, greater than about 300 separate ratios can be resolved within the binary $A_xB_{1-x}$ ($0 \leq x \leq 1$), as shown in FIG. 2.

The RUP host materials fabricated for this example comprised either $(Y_{0.8}Yb_{0.19}(RE)_{0.01})_2O_2X$, where X was either O or S, with the rare earth emitters being either Tm for X=S and Er for X=O and Yb acting as a sensitizer for 980 nm excitation. For the studies to establish the compositional resolution that could be optically determined, physical mixtures of standards were prepared from bulk solid state samples of $(Y_{0.8}Yb_{0.19}Tm_{0.01})_2O_2S$ (labeled as rare earth "A" in FIG. 2) and $(Y_{0.8}Yb_{0.14}Er_{0.06})_2O_3$, (labeled as rare earth "B" in FIG. 2). These compounds were weighed together in the appropriate ratios and thoroughly mixed. The ratios were obtained by integrating the appropriate spectral regions for the two emitters and calculating the emission ratio for each mole or weight ratio.

Figure 2:
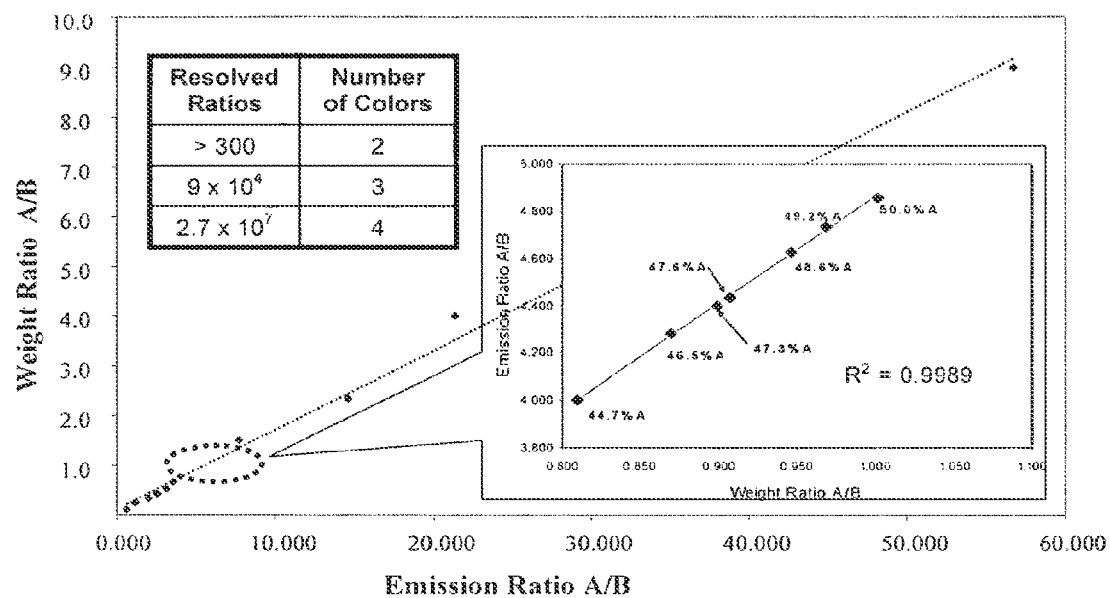
FIG. 2 shows the composition dependence of integrated intensities of Tm and Er emitters.

The compositional dependence of the integrated intensities of select regions of the Tm and Er emitters are also shown in FIG. 2. An integrated intensity data point was obtained by selecting the range within which the integration will be performed. The percent coefficient of variance (% CV) for these values were generally <0.2% of the integrated intensity values demonstrating that it will be possible to determine the A/B composition ratio from two RUP materials at least at a resolution of 0.3 wt %. If the other rare earth emitter ratios can be measured at a comparable resolution, and if the absolute intensities of the ratios can be measured with a similar accuracy, then it would be possible to multiplex ~90,000 objects or samples with three colors, about $3 \times 10^7$ with four colors and about $6 \times 10^9$ samples with five colors

Example 2

Two or More Rare Earth Emitters within One Host Phase

In the following examples, samples were measured by illuminating the Yb containing materials with a 980 nm diode laser) and collecting the emitted light in the 350-800 nm range with a fiber coupled spectrometer.

In this example, an optical barcode based on $Y_2O_3$ may be prepared with the yttrium site in the host lattice partially substituted with Yb, Tm and/or Er. In this case $Y_2O_3$ is the host lattice, host phase or host material, Yb is the absorber of the 980 nm (including nearby wavelengths as well) infrared photons, and Tm and Er are the emitters of the visible photons. A series of RUP barcodes could be prepared containing many Tm/Er ratios within a single host lattice. One such composition may be $(Y_{0.80}Yb_{0.18}Er_{0.01}Tm_{0.01})_2O_3$ and another in the series of compositions might be $(Y_{0.80}Yb_{0.18}Er_{0.0095}Tm_{0.0105})_2O_3$. To prepare this particular sample, a mixture of Y, Yb, Tm and Er oxides are thoroughly ground together for several hours in a ball mill, followed by heating from 1200-1400° C. The samples are ground again and reheated until the reaction is complete. Alternatively the materials can be prepared by one of the solution thermolysis methods discussed above. It will be understood by those skilled in the art that there are many other ratios, in addition to the two ratios demonstrated here, which may be used to identify a particular sample. The number of samples which can be distinguished using a ratio of two components depends on the resolution, accuracy and repeatability of the technique used to measure the ratio. Additional rare earth cations can be added to further increase the number of individual samples that can be encoded; for example, three components can be incorporated, as in $(Y_{0.80}Yb_{0.17}Er_{0.01}Tm_{0.01})_2O_2S$, to further increase the number of samples that can be encoded. It is clear to those skilled in the art that many other rare earth emitters in many varying ratios lay within the scope of this type of material.

Example 3

More than One Rare Earth Emitter within More than One Host Phase

A ratio of two or more RUP materials, each consisting of a different, single rare earth emitter within a host material, can also be prepared. While the rare earth emitters must be different in order to create a ratio of two emitting species, the host materials in which the individual emitters reside may the same or different host materials. An example of this type of barcode is a physical mixture of $(Y_{0.80}Yb_{0.18}Er_{0.01}Tm_{0.01})_2O_3$ and $(Y_{0.80}Yb_{0.18}Ho_{0.01}Pr_{0.02})_2O_2S$ in varying ratios to give a series of codes. By adjusting the amounts of the two materials any arbitrary ratio may be prepared. It is also clear that three or more components can be added to each material to further increase the number of samples that can be encoded by this method. An example of this type of three emitter barcode would be a physical mixture of $(Y_{0.80}Yb_{0.18}Er_{0.01}Tm_{0.01})_2O_3$ and $(Y_{0.80}Yb_{0.18}Ho_{0.01}Pr_{0.005}Dy_{0.005})_2O_2S$.

Example 4

Combination of Visible or Ultraviolet Excited Phosphors or Dyes or Quantum Dots with the RUP Materials The degree of sample multiplexing can be further increased by using another absorber/emitter in combination with the RUP materials to encoded samples. For example, if samples were encoded with an organic dye that is excited at 500 nm and emits at 600nm and since there is no emission from the RUP materials upon excitation with visible wavelengths such as 500 nm, the number of individual barcodes for a group of samples increases by a factor of two based on whether the organic dye is present or absence. An example would be a porphyrin dye that is excited in the UV and emits in the visible combined with the aforementioned RUP materials. Clearly, if the alternative dye can be distinguished more accurately than simply on and off relative to the RUP barcodes, the degree of multiplexing increases further still.

Example 5

Preparation of Combinatorial Continuous Gradient Libraries and Measuring Emitter Ratios in a Four Color System: Layered Lanthanide Materials The libraries are prepared by depositing many thin gradient layers of the appropriate oxides to make the final compositions. There are several advantages for the synthesis and evaluation of the libraries prepared by the vapor deposition method and several factors should positively influence suitability of these thin films for the statistical validation experiments: (a) the composition is very well known as a function of location on the library because of the precisely linear motion of the shutter creating the gradient during deposition; (b) the composition gradient can be physically enlarged or reduced in size (i.e., spread out on the substrate); (c) the films are extremely smooth; (d) since the thickness is very well known and controllable, quantitative values can be obtained for absorptivity and emissivity; (e) the extremely smooth film limits diffuse scatter and provides a more reproducible surface; (f) in a continuously changing composition spread, many more compositions are present than in a discrete, fixed composition library.

The libraries are fabricated in a PLD or sputtering apparatus which contains linear motion shutters, a rotating target carousel (PLD) or separate targets (sputtering) and the ability to rotate the substrate about an axis perpendicular to the plane of the substrate. Ultraviolet pulses from a xenon difluoride excimer laser ablate plumes from the targets, of composition very similar to that of the target, which deposit on the substrate after interacting with the shutter and mask. Since the deposition flux is uniform in terms of aerial homogeneity and directionality, and the shutter moves with a precisely linear motion, the composition of the libraries as function of library location is well known.

Four targets, namely $(Y_{0.8}Yb_{0.17}(RE)_{0.03})_2O_3$ with RE=Tm, Er, Ho, and Pr, are placed on the carousel. The targets are prepared by grinding $Y_2O_3$, $Yb_2O_3$ and the appropriate $(RE)_2O_3$ oxide (RE=Tat, Er, Pr, Ho), firing at 1350° C. overnight and repeating the process three more times to ensure homogeneity. After determining phase purity by XRD the samples are isostatically compacted at 600° C. and ~30 tons pressure to form the PLD or sputtering targets. Shutters are defined here as solid objects while masks contains apertures. A mask with a triangular aperture is placed in between the deposition source and the substrate as the material of interest is deposited. In the absence of a shutter the material deposited on the substrate has a uniform thickness profile. Hence the deposition scheme employed here uses a shutter with z motion placed over a stationary mask and substrate (or vice versa) as shown.

While the deposition of material A (blue) is in progress, the shutter is moved slowly in the x direction until it covers the entire aperture. A deposit with a gradient is formed. Next, the source of deposition is shut off; the shutter is moved back to its initial position in the -x direction, and the substrate is rotated by 120° with respect to an axis perpendicular to the plane of the substrate. The second deposition source (material B, green) is then started and the shutter is again moved slowly in the x direction. This produces the layers of the two materials in the desired 120° wedge orientation. This process is repeated again for depositing the third material C (red) giving rise to a ternary library, where the three wedges are oriented 120° with respect to each other. After depositing a suitable number of layers by alternating the three sources each library optically constitutes a ternary phase diagram with respect to the overall layer composition.

To determine the resolution at which the ratios of the RUP emitters are determined the same well known oxide host with the same sensitizers, namely $(Y_{\sim 0.80}Yb_{\sim 0.195}(RE_{0.005})_2O_3$, RE=Tm, Pr, Ho and Er are used in all cases. First, four continuous ternary phase diagrams are prepared each with three of the four Tar, Pr, Ho and Er emitters to give the four Tm—Pr—Ho, Tm—Pr—Er, Pr—Ho—Er and Tm—Ho—Er ternary libraries. This allows the direct experimental determination of the optical response for an arbitrary ternary ratio mixture in a library as discussed below. Since these libraries can easily be dimensionally expanded (i.e., the same composition gradient spread over a larger area) by simply changing the relative thickness of the deposited layers, any compositional region of the phase diagram can be zoomed and magnified. Therefore, the continuous gradient libraries allow an exact determination of the accuracy to which the ratios can be measured. By measuring the standard deviations on a series of measurements for a given ratio, it is possible to place boundaries on the lowest resolvable limit of the ratio.

The overall standard deviation for a ternary library, $\sigma_{overall-3}$, is calculated from the standard deviations of the constituent binary ratios $\sigma_{overall-3}=[(\sigma_{A/B})^2+(\sigma_{A/C})^2+(\sigma_{B/C})^2]^{1/2}$. The standard deviation for the quaternary library is $\sigma_{overall-4}=[(\sigma_{A/B})^2+(\sigma_{A/C})^2+(\sigma_{A/D})^2+(\sigma_{B/C})^2+(\sigma_{B/D})^2+(\sigma_{C/D})^2]^{1/2}$. By measuring the magnitude of $\sigma_{overall-4}$ for each 10% increment in D compositions in the quaternary system, one can determine the level of differentiation for individual 4-color barcodes.

To determine the optical properties of the combinatorial RUP libraries prepared as described above, the emission under 980 run excitation is determined as a function of the library address. With the aid of a programmed x-y stage the samples are automatically measured by translating the library beneath a reflection probe with initial library sizes of ~25×25 mm².

This encoding scheme has a series of degenerate codes that cannot be distinguished (e.g., 1111 vs. 2222) without the absolute determination of the integrated intensities or the amount of an internal standard unless the absolute value of the RUP samples can be determined One means of addressing this issue, all emission peaks are referenced to the 800 nm emission from the Tm emitter. This 800 nm emission is ~100 times more intense than the visible emission from any RUP materials.

Example 6

Flow Cytometric Apparatus to Read the RUP and Other Barcodes

To sort this large number of individually encoded samples, and to measure the optical barcodes at a very high rate, a technique such as flow cytometry is employed. The particles or encoded samples flow past a detector which directs them to the appropriate storage bin based on their optical signal. In order to multiplex samples with different optical reporters, different illumination and detector systems corresponding to the excitation and emission wavelengths of interest must be used. In Example 3 above, both a RUP and visible detector excitation/emission system would be employed.

Example 7

Emplying RUP-Based Optical Barcodes to Perform a Gene Expression Experiment

A description of using the present embodiments to perform a function similar to that of a DNA microarray is given in this example. One use of a DNA microarray is to monitor gene expression. Currently, the DNA sample in a microarray is in the form of a small spot of DNA (75-150 microns) whose identity is known from its location (address) on the substrate. This is a laborious, sensitive and time consuming procedure to print and process these slides. The slides are probed with two types of DNA (control labeled red and sample labeled green) and the test is evaluated by the ratio of red to green in each sample. The present invention will allow an easier, less expensive, less time consuming and potentially more accurate method to obtain the same information.

This example addresses how to prepare and evaluate a sample containing 10,000 DNA samples. An RUP system, which contains a suitable internal standard, could range from a single RUP host material with variable amounts of four different emitters to a mixture of four different RUP materials. The 9999 beads or particles are prepared where each of the four emitters is present in increments of 10% relative to the internal standard. Thus, each of the four emitters can have ten concentrations values between zero and one in 10% increments corresponding to the ten digits zero through nine sufficient to differentiate the 10,000 samples. Each could have an identifier (or code) such as 3256, which would correspond to the emitters A, B, C and D in ratio of 3:2:5:6 relative to an internal standard.

Next, 10,000 different beads, or particles of the RUP materials themselves, are prepared and 10,000 different single strand oligonucleotides, each corresponding to a particular gene or sequence of interest, are attached to the beads such that single known oligonucleotide is associated with single known bead composition. Therefore a given nucleotide can be identified from the optical signature of the particle to bead or particle to which is it attached.

As in the currently performed microarray experiments, the test and control probe DNA are labeled with two different dyes but then the probes DNA is mixed with the RUP encoded beads instead of hybridized to the DNA samples on a slide. Using a bead or cell sorter, a flow cytometer or a device with a similar function, the beads or particles with the desired hybridization behavior are separated and identified and the organic dyes and RUP emissions are temporally resolved as described above. The oligonucleotides in each of the latter samples are thus identified by the optical signature from their unique RUP. Therefore which genes or sequences were over or under expressed in the original sample can be determined. The underlying microarray experiment is the same except that the sample is identified by its RUP optical barcode rather than by its physical location on the microarray slide.

Many modifications of the exemplary embodiments of the invention disclosed above will readily occur to those skilled in the art. Accordingly, the invention is to be construed as including all structure and methods that fall within the scope of the appended claims.

What is claimed is:

1. A method of optically encoding an object, wherein the method comprises:
    combining the object with a composition comprising two or more lanthanide materials, wherein each lanthanide material comprises a host, an absorber and one and more emitters, and wherein the lanthanide materials emit detectable electromagnetic radiation upon excitation with absorbable electromagnetic energy;
    irradiating the object with radiation having a wavelength greater than 800 nm, thereby inducing emission from the emitters at a radiation wavelength less than 800 nm, wherein each emitter emits at a different wavelength;
    measuring relative integrated emission intensities from the emitters within a different wavelength range for each emitter;
    calculating relative ratios of the integrated emission intensities from the emitters, the relative ratios comprising resolvable ratios;
    calculating a number of optical codes C, the number of optical codes C being equal to $R^{M-1}$, where R is the number of the resolvable ratios and M is the number of the emitters in the two or more lanthanide materials;
    assigning a unique optical code to each calculated relative ratio; and
    processing the unique code to identify the object.

2. The method according to claim 1, wherein the host of at least one of the two or more lanthanide materials comprises an oxide, oxysulfide, aluminate, gallate or halide.

3. The method according to claim 1, wherein the host of at least one of the two or more lanthanide materials is selected from a group consisting of sodium yttrium fluoride, lanthanum fluoride, lanthanum oxysulfide, yttrium oxysulfide, yttrium fluoride, yttrium gallate, yttrium aluminum garnet, gadolinium fluoride, barium yttrium fluoride, and gadolinium oxysulfide.

4. The method according to claim 1, wherein the absorber of at least one of the two or more lanthanide materials is selected from the group consisting of ytterbium, erbium and samarium.

5. The method according to claim 4, wherein each of the lanthanide materials further comprises at least one emitting center selected from a group consisting of erbium, holmium, terbium, thulium, praseodymium, neodymium and dysprosium.

6. The method according to claim 5, wherein the molar ratio of absorber to emitting center is between 1:1 and 2000:1.

7. The method according to claim 5, wherein the at least one emitting center is erbium, and wherein the molar ratio of absorber to emitting center is between 20:1 and 100:1.

8. The method according to claim 4, wherein each of the lanthanide materials further comprises at least one emitting center selected from a group consisting of thulium, praseodymium, neodymium, dysprosium and holmium.

9. The method according to claim 8, wherein the molar ratio of absorber to emitting center is between 500:1 and 2000:1.

10. The method according to claim 1, wherein the materials are irradiated using an infrared laser diode or an incandescent filament.

11. The method according to claim 1, wherein the emission intensities are measured using a photomultiplier device, avalanche photodiode, a charge-coupled device, a CID device, a photographic film emulsion, a photochemical reaction yielding detectable products, or through visual observation.

12. The method according to claim 1, wherein the object is a probe.

13. The method according to claim 1, wherein the object is a paper document or optical medium.

14. The method according to claim 1, wherein the object is an organic molecule.

15. The method according to claim 1, wherein at least one of the lanthanides is in the form of a colloidal suspension.

16. The method according to claim 1, where the object is a DNA, RNA or polynucleotide molecule.

17. The method according to claim 1, where the object is a glass or polymer bead or microsphere.

18. The method according to claim 1, where the object is a glass, polymer bead, or microsphere coated with DNA, RNA, or a polynucleotide.

19. The method according to claim 1, where the object is a glass, polymer bead, or microsphere coated with a protein, a polypeptide, or an antibody.

20. The method according to claim 1, wherein at least one of the two lanthanide materials is in the form of a solid solution wherein the one or more emitters are randomly and isomorphously incorporated into the host of the solid solution.

21. A method of uniquely identifying an object, wherein the method comprises the steps of:
    combining the object with a composition comprising at least two lanthanide materials, wherein each of the lanthanide materials comprises at least one host lattice, at least one absorber, and at least one emitter, wherein the emitters of the lanthanide materials emit at different wavelengths;
    irradiating the composition with absorbable electromagnetic radiation, thereby inducing emission from the emitters;
    measuring a first emission intensity of emission from the at least one emitter of one of the at least two lanthanide materials and a second emission intensity of emission of the at least one emitter of another one of the at least two lanthanide materials;
    calculating a first ratio of the first emission intensity to the second emission intensity, wherein the first ratio calculated in the calculating step comprises one of a number of resolvable ratios;
    uniquely identifying the object from the calculated ratio; and
    calculating a number of optical codes C, the number of optical codes C being equal to $R^{M-1}$, where R is the number of the resolvable ratios and M is the number of the emitters in the at least two lanthanide materials.

22. The method according to claim 21, wherein:
    at least one of the at least two lanthanide materials includes a second emitter;
    the measuring step further includes measuring a third emission intensity of the second emitter;
    the calculating step further includes calculating a second ratio of the first emission intensity to the third emission intensity and calculating a third ratio of the second emission intensity to the third emission intensity; and
    at least one of the second and third ratios defining further resolvable ratios.

23. The method according to claim 21, wherein:
    the composition comprises at least a third lanthanide material which includes at least one emitter;
    the measuring step further includes measuring a third emission intensity of the at least one emitter of the third lanthanide material;
    the calculating step further includes calculating a second ratio of the first emission intensity to the third emission intensity and calculating a third ratio of the second emission intensity to the third emission intensity; and
    at least one of the second and third ratios defining further resolvable ratios.

24. A method of identifying an object, wherein the method comprises the steps of:
    combining the object with a lanthanide material comprising at least one host, at least one absorber, and at least first and second emitters, wherein the first emitter emits at a different wavelength than the second emitter;
    irradiating the lanthanide material with absorbable electromagnetic radiation, thereby inducing emission from the first and second emitters;
    measuring a first emission intensity of emission from the first emitter and a second emission intensity of emission from the second emitter;
    calculating a first ratio of the first emission intensity to the second emission intensity, wherein the first ratio calculated in the calculating step comprises one of a number of resolvable ratios;
    identifying the object from the first ratio; and
    calculating a number of optical codes C, the number of optical codes C being equal to $R^{M-1}$, where R is the number of the resolvable ratios and M is the number of the emitters in the lanthanide material.

25. The method according to claim 24, wherein:
    the lanthanide material includes at least a third emitter;
    the measuring step further includes measuring a third emission intensity of the third emitter;
    the calculating step further includes calculating a second ratio of the first emission intensity to the third emission intensity and calculating a third ratio of the second emission intensity to the third emission intensity; and
    at least one of the second and third ratios defining further resolvable ratios.

* * * * *